Figure 2:
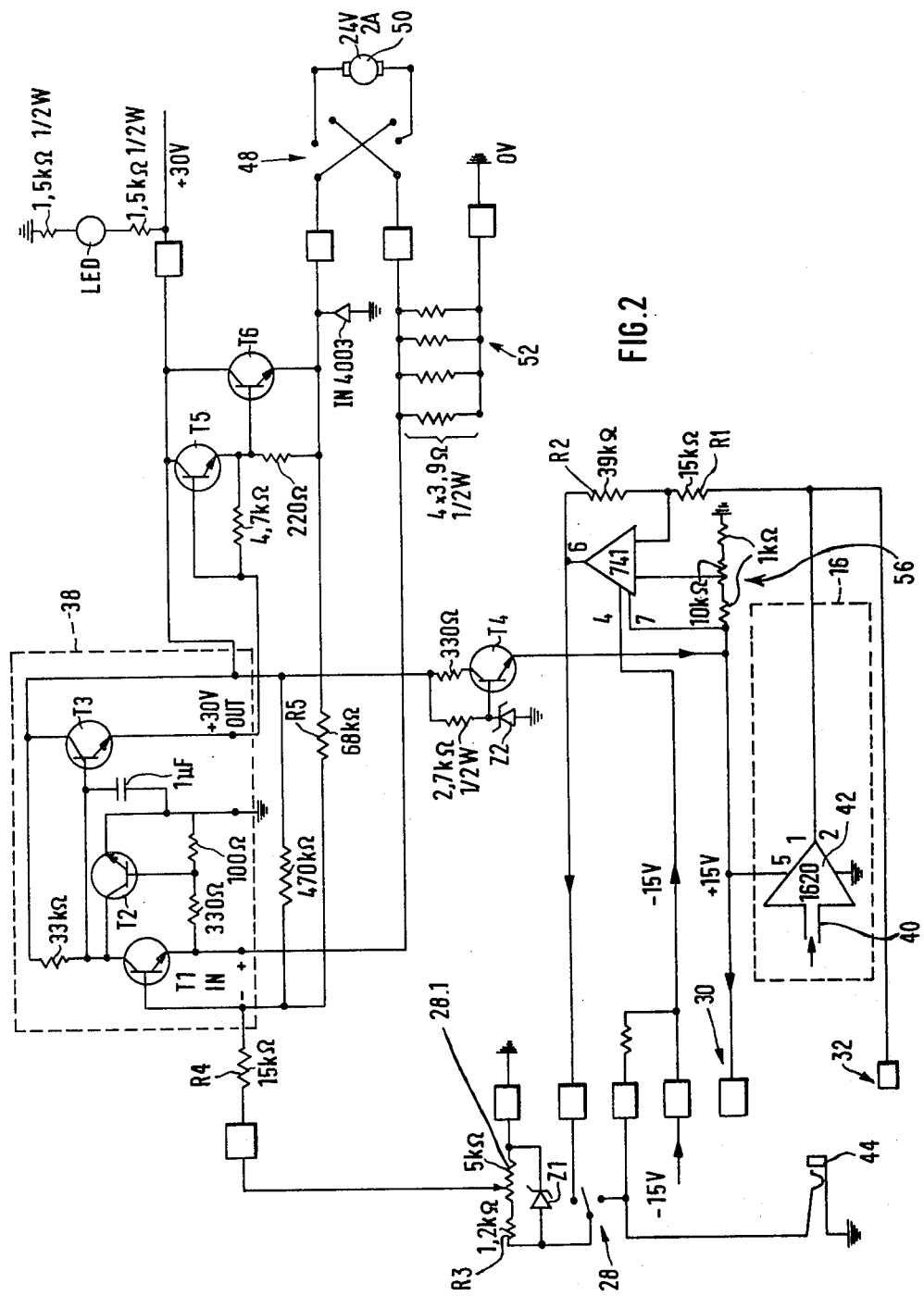

United States Patent [19]

Samuels et al.

[11] 4,256,998

[45] Mar. 17, 1981

[54] ELECTRICAL CONTROL ARRANGEMENT

[76] Inventors: Basil J. Samuels, Xanadu, Strawberry Hill, Constantia 7800; Johann L. N. Besseling, Mayville, Nursery Rd., Rosebank 7700, both of South Africa

[21] Appl. No.: 72,468

[22] Filed: Sep. 4, 1979

Related U.S. Application Data

[63] Continuation of Ser. No. 859,527, Dec. 12, 1977, abandoned.

[51] Int. Cl.³ .............................................. H02P 5/16
[52] U.S. Cl. .................................... 318/335; 318/481; 318/645; 433/101
[58] Field of Search ................ 318/335, 481, 17, 646, 318/645; 32/26, 27; 73/199; 310/50

[56] References Cited

U.S. PATENT DOCUMENTS

| 3,427,720 | 2/1969 | Berman et al. | 32/27 |
| 3,567,330 | 3/1971 | Apelskog et al. | 32/27 |
| 3,604,960 | 9/1971 | Krestel | 310/50 |
| 3,633,420 | 1/1972 | Holzem | 318/335 |
| 3,959,883 | 6/1976 | Walls et al. | 32/27 |
| 4,026,027 | 5/1977 | Kokal, Jr. | 32/26 |

Primary Examiner—David Smith, Jr.
Attorney, Agent, or Firm—Diller, Ramik & Wight

[57] ABSTRACT

An electrical control arrangement which includes firstly an electronic transducer, which is adapted to receive a controlled stream of fluid, and secondly control means to be controlled by the electronic transducer to control the speed of a micro-motor in a linear manner.

7 Claims, 5 Drawing Figures

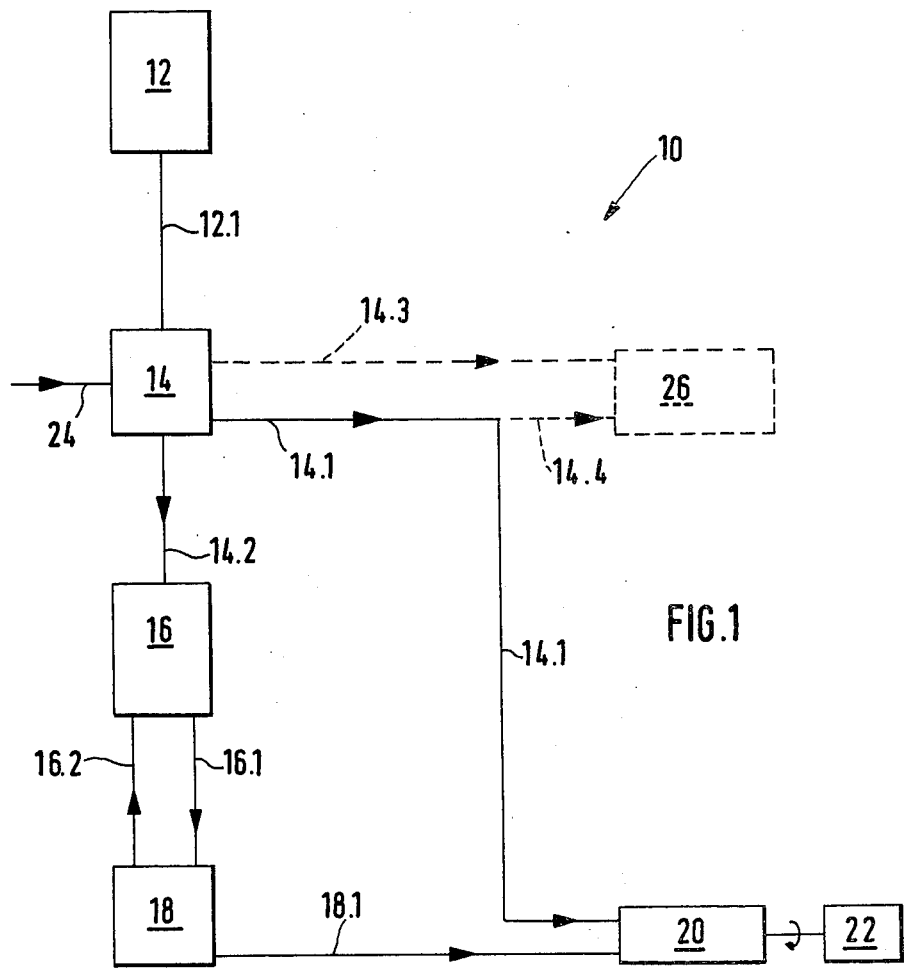
FIG.1
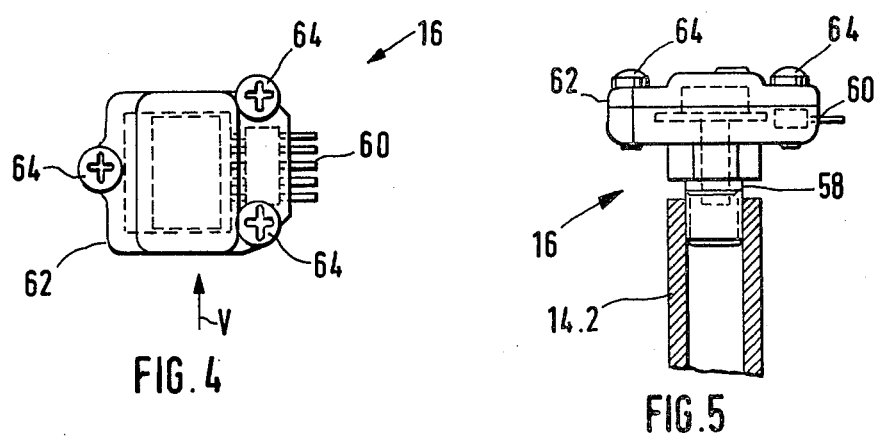
FIG.4
FIG.5 ly of fluid, such as air, and control means adapted to be controlled by the electronic transducer so as to control the speed of a micro-motor in a linear manner.
ELECTRICAL CONTROL ARRANGEMENT This is a continuation of application Ser. No. 859,527 filed Dec. 12, 1977, now abandoned.

BACKGROUND OF THE INVENTION

1. Field of the Invention:

The present invention is in the field of an improved electrical control arrangement, and in particular for controlling micro-motors.

A major problem associated with micro-motors, particularly for use in dental equipment, is that such motors are not controllable in a linear manner.

2. Prior Art

Various control arrangements are known but none suggest a linear control of micro-motors.

SUMMARY OF INVENTION

In accordance with the invention an electrical control arrangement is provided with an electronic transducer which is adapted to receive a controlled stream of fluid, such as air, and control means adapted to be controlled by the electronic transducer so as to control the speed of a micro-motor in a linear manner.

The arrangement also may include a manually operable control device; a solid state module; an electronic torque control unit; and a micro-motor which is adapted to drive a handpiece. The manually operable control device is adapted to supply air to the solid state module. The solid state module is adapted to supply air to the electronic transducer, and also to supply a coolant received by it to the micromotor. The electronic transducer is adapted to control the electronic torque unit for varying the speed of the micro-motor in a linear manner.

The arrangement may also include a high speed tool which is adapted to be driven by air from the solid state module, and coolant may be supplied to the high speed tool from the solid state module.

In the case of dental equipment the handpiece and the high speed tool may be dental drills. The manually operable device may include a foot control unit.

Also according to the invention a method of electrical control of a system includes an electronic transducer and control means, which comprises the step of providing a controlled stream of fluid, such as air, to the electronic transducer and allowing the electronic transducer to control the control means for controlling the speed of a micro-motor in a linear manner.

Here the step is provided of controlling the solid state module by manually controlling an air supply to the solid state module and thus controlling the fluid pressure to the electronic transducer.

Other features and advantages of the invention will be set forth in, or be apparent from the detailed description of a preferred embodiment found hereinbelow.

In the drawings there is shown in

Figure 3:
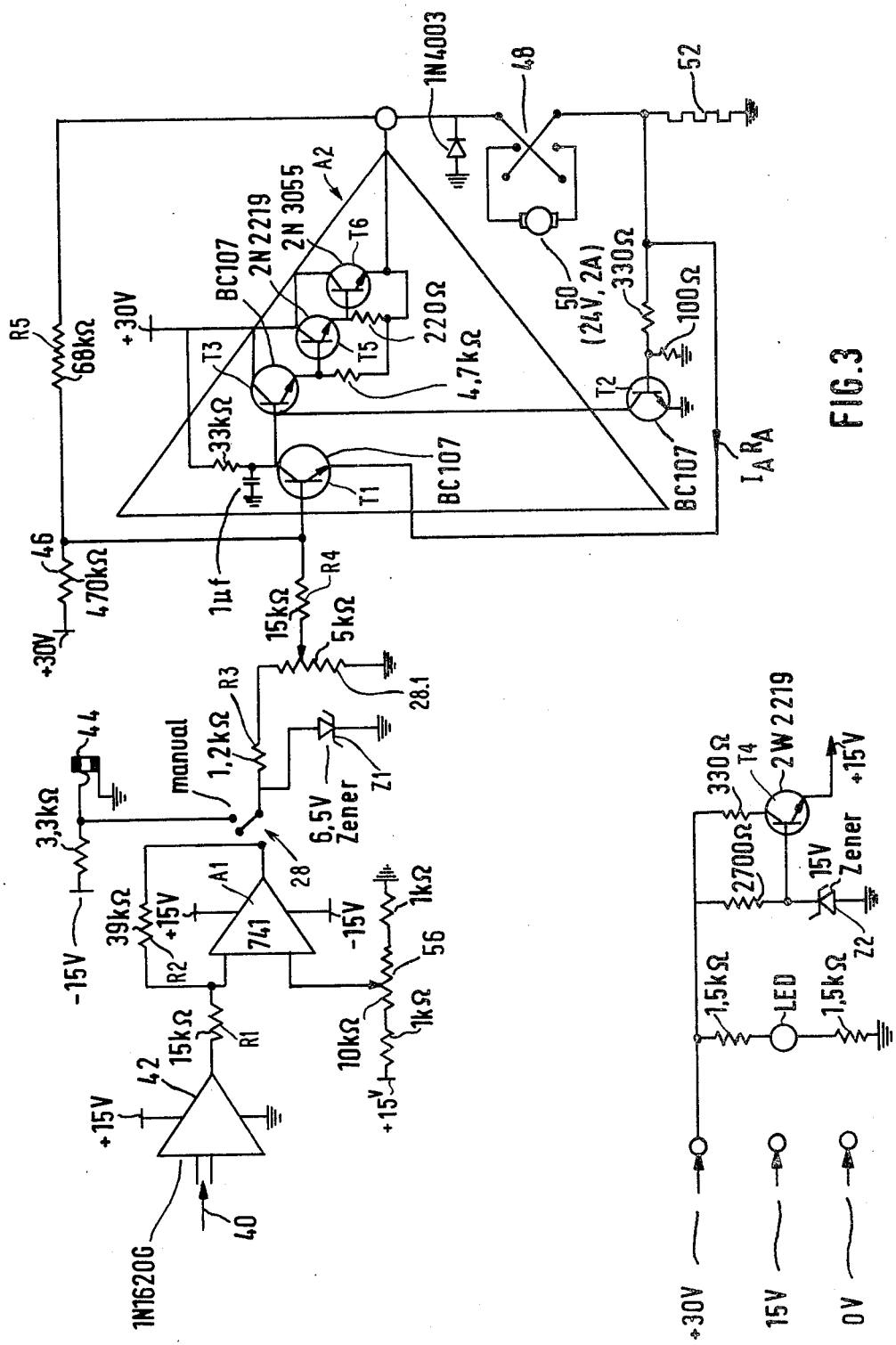

FIG. 1 a block diagram of the electrical control unit in accordance with the invention;

FIG. 2 a first representation of an electronic circuit diagram of the electrical part of the electrical control unit;

FIG. 3 a second representation of an electronic circuit diagram of the electrical part of the electrical control unit;

FIG. 4 a plan view of a typical electronic transducer mounting; and

FIG. 5 a side view of the electronic transducer seen along arrow V in FIG. 4.

Referring to FIG. 1, the electrical control unit 10 includes a manually operable control device in the form of a foot control device 12, a solid state module 14, an electronic transducer 16, an electronic torque control unit 18 and a micro-motor 20, having a handpiece 22 coupled directly to it.

The foot control unit 12 is adapted to supply air along conduit 12.1 to the solid state module 14. The solid state module 14 receives water coolant from a supply 24 and supplies the water coolant via conduit 14.1 to the micro-motor 20 (and handpiece 22). Furthermore, the solid state module 14 supplies air for controlling the electronic transducer 16. This supply of air is via conduit 14.2. Control current is supplied via conductors 16.1, 16.2 to the unit 18 and the electronic transducer 16 electronically controls the electronic torque control unit 18, which in turn, via current supplied via conductors 18.1, varies the speed of the micro-motor 20 in linear manner.

The electronic transducer, in one commercially available form, includes basically a linear circuit and consists essentially of a Wheatstone-bridge arrangement of four piezoresistors diffused into a silicon chip 42 (see FIGS. 2 and 3). Details of a typical housing are given in FIGS. 4 and 5.

The speed of the micro-motor can vary between 0 and 120,000 r.p.m. Furthermore, the electronic torque control unit 18 may have a selector to select various speeds which in turn can be varied by means of the foot control 12.

A further high speed handpiece 26 can also be provided. This may be driven by air via conduit 14.3 off the solid state module 14. Coolant is also supplied to it via conduit 14.4. The speed of such a handpiece may be between 250,000-500,000 r.p.m.

The electrical control unit in accordance with the invention is particularly intended for controlling hand tools (i.e. drills) in dental equipment. By means of the foot control device 12 a dentist thus can control the speed of the handtool 22 in a linear manner, and also another handpiece 26 can be controlled and driven directly by means of an air supply.

Referring simultaneously to FIGS. 2 and 3 which illustrate the same circuitry but in different arrangements, the foot pedal air control delivers air at 40 to the input port of the transducer 42, the air pressure being variable between 0 and 1.75 kg/cm². The output of the transducer correspondingly varies linearly between 2.5-5 Volts and is applied through the resistor R1 as one input to the differential amplifier A1 whose other input is at reference voltage level as established by setting of the potentiameter 56 of the illustrated voltage dividing resistor chain. The purpose of the amplifier A1 is to increase the voltage swing produced at the output of the transducer 42, while preserving the linearity thereof by means of the feedback resistor R2. The output 6 of the amplifier A1 may be connected by means of the manual switch 28 to the amplifier circuit A2, whose input is formed by the divider chain R3, 28.1 and protective Zener diode Z1. The movable tap of the potentiameter 28.1 is adjusted to obtain a voltage swing of 0-6.5V corresponding to the 2.5-5.0V swing of the transducer 42.

The first stage of the amplifier A2 is formed by the transistor T1 whose base electrode is biassed through the divider chain 46, R4 and 28.1, as influenced by the output of the amplifier A1. The output of the amplifier A2 is connected back to its input by means of the feedback resistor R5 and a second feedback loop is formed by the transistor T2 whose emitter-collector path is connected to the base electrode of the first state T3 of the cascade arrangement T3, T5, T6 which is driven by the input stage T1.

The motor 50 is connected, through the reversing switch 48 to ground through the shunt resistance 52. The resistance 46 corrects the offset in transistor T1. The control current for the motor 50 is established by the amplifier A2 and is such as tends to so vary the torque produced by the motor 50 as to maintain the speed linearly on demand by the foot pedal control, i.e., linear with respect to the air pressure at 40, despite variations of torque loading imposed upon the motor 50.

The switch 28 may also be positioned to connect the electrical foot control device 44 in circuit to the amplifier A2.

"Power on" is indicated by the light emitting diode LED and, as will be seen, the purpose of the transistor T4 is merely to provide, in conjunction with the Zener diode, a source of +15V.

Various electronic elements as indicated in FIG. 2 are provided in a separate board in casting resin 38.

Generally the various electronic elements have the following commercial references:

$T_1, T_2, T_3 = BC107B$
$T_4, T_5 = 2N2219A$
$T_6 = 2N3055$
$Z_1 = BZY BB6.5V ZENER$
$Z_2 = BZY94 15V ZENER$

40: air from supply pedal (0-1.75 kg/cm$^2$).
42: 1X 1620G
44: external footswitch
46: resistance setting starting point
48: reversing switch
50: motor
52: shunt (1 Ω)
54: supplies from power pack
56: Trim In FIGS. 4 and 5 a typical electronic transducer 16 is shown. It has an air supply tube 58 to which a air supply pipe (e.g. 14.2 of FIG. 1) is attached. Electrical connections to a current source and to the electronic torque control unit (18 in FIG. 1) are by way of a removable plug and socket arrangement 60. The housing 62 of the transducer has screw connections 64 to mount it suitably.

We claim:
1. An electrical control arrangement which includes
(a) a manually operable control device;
(b) a solid state module;
(c) an electronic transducer;
(d) an electronic torque control unit;
(e) a micro-motor;
(f) driving means for drivingly connecting the micro-motor to a hand piece;
(g) a first fluid supply conduit for supplying fluid from the control device to the solid state module;
(h) a second fluid supply conduit for supplying fluid from the solid state module to the electronic transducer;
(i) a first coolant supply conduit for supplying a coolant to the solid state module;
(j) a second coolant supply conduit for supplying the coolant from the solid state module to the micro-motor;
(k) connection means for electrically connecting respectively the electronic transducer to the electronic torque control unit, and the electronic torque control unit to the micro-motor, the electronic transducer being controllable by the manually operable control device which controls the fluid flow to the electronic transducer via the solid state module, the electronic torque control unit being controllable by the electronic transducer; and the speed of the micro-motor being variable in linear manner by the current supply from the electronic torque control unit.

2. A control arrangement as claimed in claim 1, in which the first fluid supply conduit is adapted to supply air.

3. A control arrangement is claimed in claim 1, which additionally includes a fluid driven high speed tool, and in which a third fluid supply conduit is provided for supplying fluid from the solid state module to the high speed tool.

4. A control arrangement as claimed in claim 3, in which a third coolant supply conduit is provided for supplying coolant from the solid state module to the high speed tool.

5. A control arrangement as claimed in claim 1, in which the hand piece is a dental drill.

6. A control arrangement as claimed in claim 3, in which the high speed tool is a dental drill.

7. A control arrangement as claimed in claim 1, in which the manually operable control device includes a foot control unit.

* * * * *

UNITED STATES PATENT AND TRADEMARK OFFICE
CERTIFICATE OF CORRECTION

PATENT NO. : 4,256,998

DATED : March 17, 1981

INVENTOR(S) : Basil J. Samuels et al.

It is certified that error appears in the above—identified patent and that said Letters Patent is hereby corrected as shown below:

On the title page add the following:
-- [30] Foreign Application Priority Data
Dec. 17, 1976      South Africa..........76/7493 --.

Signed and Sealed this

Nineteenth Day of May 1981

[SEAL]

Attest:

RENE D. TEGTMEYER

Attesting Officer      Acting Commissioner of Patents and Trademarks